(12) United States Patent
Teodorescu

(10) Patent No.: US 10,453,571 B2
(45) Date of Patent: Oct. 22, 2019

(54) EVENT DRIVEN CONFIGURATION OF A SURGICAL SYSTEM CONSOLE

(75) Inventor: Dan V. Teodorescu, Fountain Valley (CA)

(73) Assignee: Alcon Research, LLC, Fort Worth, TX (US)

( * ) Notice: Subject to any disclaimer, the term of this patent is extended or adjusted under 35 U.S.C. 154(b) by 2063 days.

(21) Appl. No.: 12/643,310

(22) Filed: Dec. 21, 2009

(65) Prior Publication Data

US 2011/0152728 A1    Jun. 23, 2011

(51) Int. Cl.
| | |
|---|---|
| *G16H 40/00* | (2018.01) |
| *G16H 40/63* | (2018.01) |
| *A61B 34/00* | (2016.01) |
| *G06F 19/00* | (2018.01) |
| *A61B 17/00* | (2006.01) |

(52) U.S. Cl.
CPC ............ *G16H 40/63* (2018.01); *A61B 34/25* (2016.02); *G06F 19/00* (2013.01); *A61B 2017/00199* (2013.01); *A61B 2034/254* (2016.02)

(58) Field of Classification Search
None
See application file for complete search history.

(56) References Cited

U.S. PATENT DOCUMENTS

| | | | |
|---|---|---|---|
| 4,933,843 A * | 6/1990 | Scheller et al. ................ 604/22 |
| 5,997,528 A | 12/1999 | Bisch et al. | |
| 6,055,458 A | 4/2000 | Cochran et al. | |
| 6,106,512 A | 8/2000 | Cochran et al. | |
| 2006/0114175 A1 | 6/2006 | Boukhny | |
| 2006/0235307 A1 | 10/2006 | Boukhny et al. | |
| 2006/0236242 A1 | 10/2006 | Boukhny et al. | |
| 2006/0248477 A1* | 11/2006 | Boukhny et al. ............. 715/840 |
| 2007/0202479 A1 | 8/2007 | Todd et al. | |
| 2008/0004728 A1 | 1/2008 | Essex et al. | |
| 2008/0177152 A1* | 7/2008 | Donofrio et al. ............. 600/300 |
| 2009/0049397 A1 | 2/2009 | Boukhny | |

FOREIGN PATENT DOCUMENTS

| | | |
|---|---|---|
| EP | 1 872 736 A2 | 1/2008 |
| EP | 1 872 736 A3 | 4/2008 |
| WO | WO 2009/023376 A2 | 2/2009 |
| WO | WO 2009/023376 A3 | 5/2009 |
| WO | WO 2011/084221 A2 | 7/2011 |
| WO | WO 2011/084221 A3 | 12/2011 |

OTHER PUBLICATIONS

International Searching Authority, International Search Report, PCT/US2010/055380, dated Oct. 21, 2011, 4 pages.
International Searching Authority, Written Opinion of the International Searching Authority, PCT/US2010/055380, dated Oct. 21, 2011, 6 pages.

* cited by examiner

*Primary Examiner* — Joseph M Santos Rodriguez

(57) ABSTRACT

The present disclosure is directed to a user interface for modifying preprogrammed relationships between a plurality of subsystems of a surgical system. The user interface may be presented on a system display screen. It includes one or more selectable triggering events shown on the display screen, with each of the one or more selectable triggering events identifying a subsystem condition that selectively occurs during a surgical procedure performed with the surgical system. The interface also includes a plurality of selectable responses to the one or more selectable triggering events. The selectable responses deviate from the preprogrammed relationships between subsystems of the surgical system.

20 Claims, 6 Drawing Sheets

EVENT DRIVEN CONFIGURATION OF A SURGICAL SYSTEM CONSOLE

FIELD OF THE INVENTION

This disclosure relates to systems and methods for configuring a surgical console to respond to an initiating event and more particularly, to systems and methods for configuring a console to respond to an initiating event occurring during a surgical procedure.

DESCRIPTION OF THE RELATED ART

Emulsification surgical systems allow a surgeon to simultaneously control multiple instruments and devices to perform an ophthalmic surgery. The instruments and devices, referred to herein as subsystems of the overall surgical system, are often electrically or pneumatically operated, with the surgical system providing electrical or fluid pressure control signals for operating the instruments. For example, some subsystems in a modern ophthalmic surgical system include an ultrasonic generator subsystem, irrigation, an aspiration pump subsystem, a pneumatic vitrectomy cutter subsystem, among others.

For simplicity of operation, some surgical systems are preprogrammed to control the functional relationships between different subsystems of the surgical system. Accordingly, in response to a single input, the surgical system may control more than one of these subsystems. This allows the operating surgeon to focus his or her attention more on the surgery, and less on controlling multiple independently but simultaneously operating subsystems.

In conventional ophthalmic surgical systems, the preprogrammed functional relationships between subsystems are hard-coded into the surgical system. For example, the system is preprogrammed so that when certain conditions are met at one subsystem, the system responds by controlling the same or another subsystem according to a preset program. This provides a level of consistency in operation among different emulsification surgical systems and can provide a level of safety as the system is unable to deviate from an established norm.

Yet as additional advances are made in emulsification surgery and in eye treatment generally, some advantages may be found in deviating the subsystem relationships from those that were hard-coded in the programming when the system was manufactured. In current systems, this can be a time consuming and tedious process because highly trained technicians must write new code and re-program the systems. This may involve upgrading the software in each system or replacing the code with the new code.

Additionally, in some instances, particular surgeons may wish to deviate the preprogrammed subsystem relationships from the hard-coded relationships in order to best match their surgical techniques and preferences with their particular style. For example, such modifications may optimize the surgeon's success while minimizing corneal burns and other undesired side effects.

In other instances, scientists using the system to develop optimizations and better, safer techniques are limited in their ability to deviate the ophthalmic surgical systems from their preprogrammed state for experimental purposes. When the scientist wants to experiment with functional relationships between subsystems that are not preprogrammed into the system, the scientist must request a new program, which then must be written and loaded onto the surgical system. Months may pass before he or she can perform the experiment. Again, this can be time consuming and tedious, slowing and delaying the advance of technology and surgical techniques.

SUMMARY

In one aspect, the present disclosure is directed to a user interface for modifying preprogrammed relationships between a plurality of subsystems of a surgical system. The user interface may be presented on a system display screen. It may include one or more selectable triggering events shown on the display screen, with each of the one or more selectable triggering events identifying a subsystem condition that selectively occurs during a surgical procedure performed with the surgical system. The interface also may include a plurality of selectable responses to the one or more selectable triggering events. The selectable responses deviate from the preprogrammed relationships between subsystems of the surgical system.

In some aspects, the user interface further includes one or more selectable ending criteria for one or more of the plurality of selectable responses. The ending criteria may identify conditions for ending the response to the triggering event and resuming control of the subsystems based on the preprogrammed relationships.

In another exemplary aspect, the present disclosure is directed to an emulsification surgical system. The system includes a first subsystem configured to perform a portion of a phacoemulsification surgery and a second subsystem configured to cooperate with the first subsystem to perform a portion of a phacoemulsification surgery. The system also includes a computer system operatively associated with both the first and second subsystems. The computer system contains preprogrammed relationships between the first and second subsystems to control the first and second subsystems during the phacoemulsification surgery. A display screen is associated with the computer system and is configured to display data relevant to the emulsification surgical system. The system includes a user interface displayable on the display screen that is configured to receive inputs that modify the preprogrammed relationships on the computer system. The user interface includes one or more selectable triggering events shown on the display screen, with each selectable triggering event identifying a subsystem condition that selectively occurs on the first subsystem during a surgical procedure performed with the surgical system. The user interface also includes a plurality of selectable responses to the one or more selectable triggering events. The selectable responses are performable by the second system and deviate from the preprogrammed relationships between the first and second subsystems.

In some aspects, the first and second subsystem are each one of: a footpedal subsystem, a fluidics subsystem, an ultrasonic generator subsystem, a vitrectomy cutter subsystem, and an intravenous (IV) pole subsystem.

In yet another exemplary aspect, the present disclosure is directed to a method of modifying preprogrammed relationships between a plurality of subsystems of a surgical system. The method includes receiving a first input from a user at a user interface. The first input may select a selectable triggering event from one or more selectable triggering events shown on a display screen on the surgical system. The selected triggering event may identify a subsystem condition that selectively occurs during a surgical procedure performed with the to surgical system. The method also may include receiving a second input from a user at the user interface. The second input may select a selectable response from a plurality of selectable responses to the one or more selectable triggering events that deviates from the preprogrammed relationships between subsystems of the surgical system.

In some aspects, the method includes receiving a third input from a user at the user interface. The third input may select one or more selectable ending criteria for one or more of the plurality of selectable responses. The ending criteria may identify conditions for ending the response to the triggering event and resuming control of the subsystems based on the preprogrammed relationships.

BRIEF DESCRIPTION OF THE DRAWINGS

Aspects of the present disclosure are best understood from the following detailed description when read with the accompanying figures.

DETAILED DESCRIPTION

Figure 1:
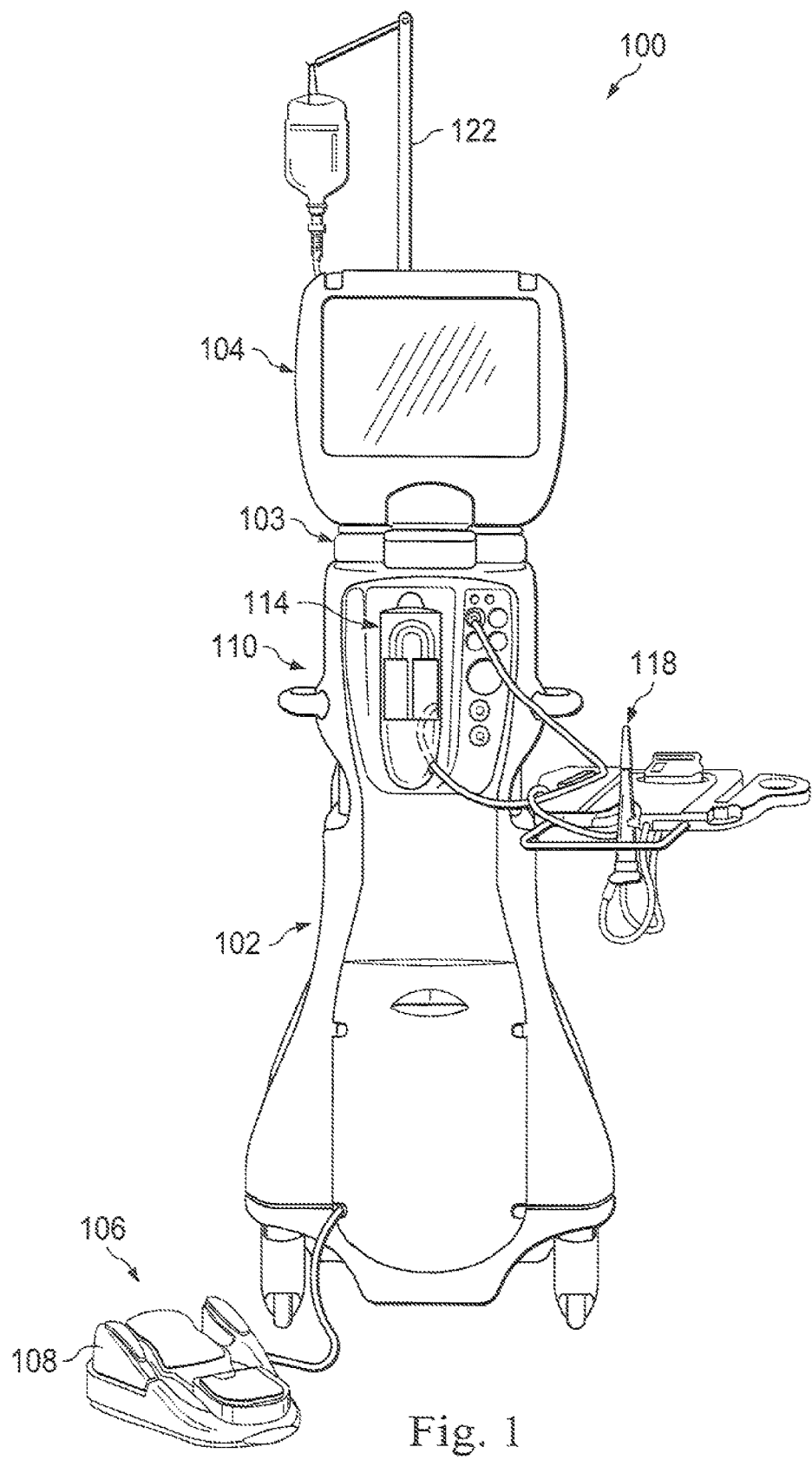
FIG. 1 is an illustration of an exemplary emulsification surgical console having a configurable console interface using the principles and methods described herein.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

In various embodiments, an interface on a system (e.g., a surgical system) may allow users (e.g., surgeons or scientists) to make modifications to relationships between subsystems. For example, the system and methods described herein may permit a user to configure an emulsification surgical console by creating customized and immediately implementable event driven console responses using a simple IF-THEN user interface. More particularly, using the IF-THEN user interface, a user can configure an emulsification surgical console to create a desired response in one subsystem as a result of an initiating event in a different subsystem. In some examples, the interface is an IF-THEN-UNTIL interface, where the console performs the desired response until specific, identifiable ending criteria are met. In this console, an IF list contains a listing of initiating events, referred to herein as triggering events. In some examples, these triggering events are categorized by subsystem. In other examples these events are categorized based on other relationships. A THEN list contains the desired actions the console can perform, referred to herein as a desired response to or result of the triggering event. Like the triggering event, these may be categorized by subsystem. An UNTIL list contains conditions or criteria for ending the response to the triggering event and returning the subsystem control to operate under the original, preprogrammed settings.

These configuration liberties enable a user to modify the relationships between different subsystems in the surgical console, thereby customizing subsystem responses and permitting a user to tailor the console operation to his or her own preferences. Accordingly, the user is empowered to control and operate the console in ways that were not conceived or considered during the design of the console.

Because the user can modify the subsystem triggering events and responses to the events, the programming delays that occur in conventional systems can be reduced and in some instances, entirely avoided. As such, users (e.g., surgeons) may now be able to adjust subsystem relationships to better tailor the relationships to their personal preferences and particular style. Likewise, users may now make system modifications to subsystem relationships for experimental purposes without relying on a programmer to prepare a new computer program to change the relationships between subsystems. Users, therefore, can more efficiently conduct experiments to find surgical optimizations, new procedures, and more efficient techniques. The systems and methods are further described below with reference to the figures of this disclosure.

Figure 2:
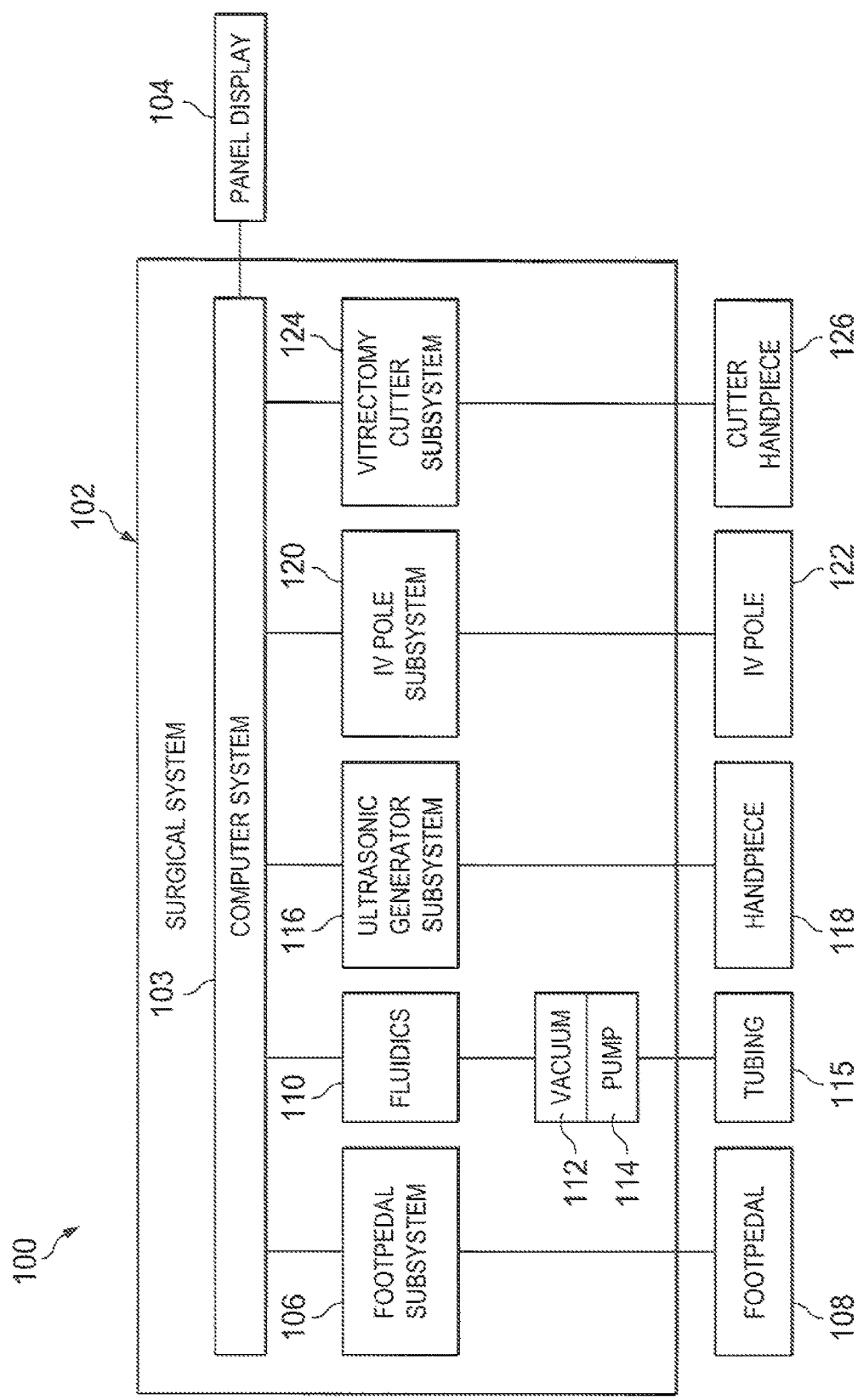
FIG. 2 is a block diagram of the exemplary emulsification surgical console of FIG. 1.

FIG. 1 illustrates an emulsification surgical console, generally designated 100, according to an exemplary embodiment. FIG. 2 is a block diagram of the console 100. The console 100 includes a base housing 102 with a computer unit 103 and an associated display screen 104 showing data relating to system operation and performance during an emulsification surgical procedure. The console also includes a number of subsystems that are used together to perform the emulsification surgical procedures. For example, the subsystems include a footpedal subsystem 106 including, for example, a footpedal 108, a fluidics subsystem 110 including an aspiration vacuum 112 and irrigation 114 that connect to tubing 115, an ultrasonic generator subsystem 116 including an ultrasonic oscillation handpiece 118, an intravenous (IV) pole subsystem 120 including a motorized IV pole 122, and a pneumatic vitrectomy cutter subsystem 124 including a vitrectomy handpiece 126. To optimize performance of the different subsystems during surgery, their operating parameters differ according to, for example, the particular procedure being performed, the different stages of the procedure, the surgeon's personal preferences, whether the procedure is being performed in the anterior or posterior portion of the patient's eye, and so on.

The different subsystems in the base housing 102 comprise control circuits for the operation and control of the respective microsurgical instruments. The computer system 103 governs the interaction and relationship between the different subsystems to properly perform an emulsification surgical procedure. To do this, it includes a processor and memory and is preprogrammed with instructions for controlling the subsystems to carry out an emulsification surgical procedure.

As shown in FIG. 1, the display screen 104 rests on the base housing 102 for viewing and access by the user. An input device permits a user to control images on the display and to make selections within a limited scope to control or modify the preprogrammed relationships between different subsystems. In this embodiment, the input device is a touch screen device responsive to selections made directly on the screen. However, other input devices, such as a standard computer keyboard, a standard pointing device, such as a mouse or trackball, or other input device are also contemplated.

In the exemplary embodiment described herein, the display screen 104 shows an exemplary user interface that permits a surgeon, scientist, or other user to use the input device to select or adjust parameters that affect the relationships between the different subsystems of the console 100. Accordingly, based on a user input, a user may change or adjust the relationships from those that were hard-coded into the console by the system programmers.

Figure 3:
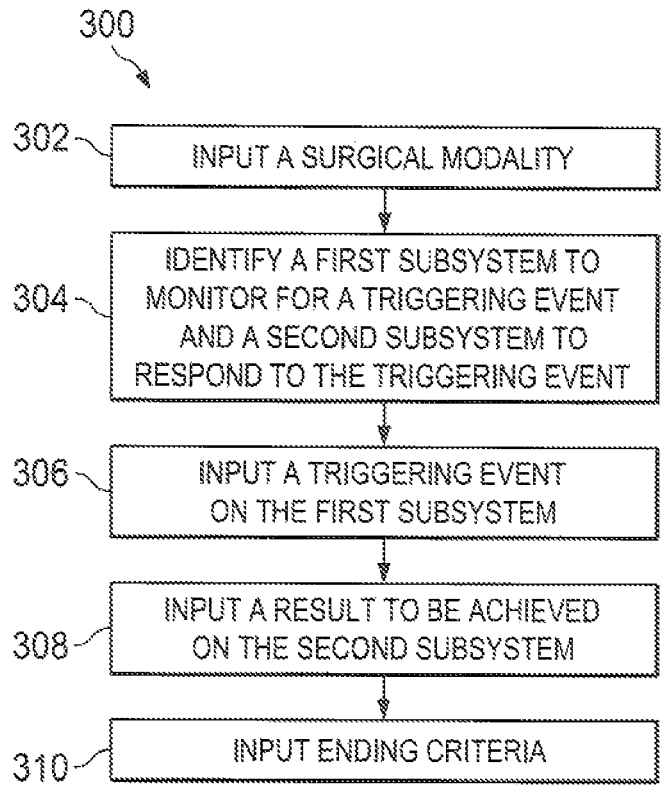
FIG. 3 is a flow diagram illustrating an exemplary method of modifying the preprogrammed operation of the emulsification surgical console of FIG. 1.

FIG. 3 is a flow diagram detailing an exemplary procedure or method 300 for adjusting relationships between subsystems on the emulsification surgical console 100 shown in FIGS. 1 and 2. This method permits a user to adjust or modify a preprogrammed relationship to achieve a specific, subsystem response to a specific subsystem initiating event to achieve a desired result. A user interface, particularly adapted to receive user inputs relating to subsystem control, may be used to carry out the method 300 for adjusting relationships between the various surgical console subsystems.

Figure 4:
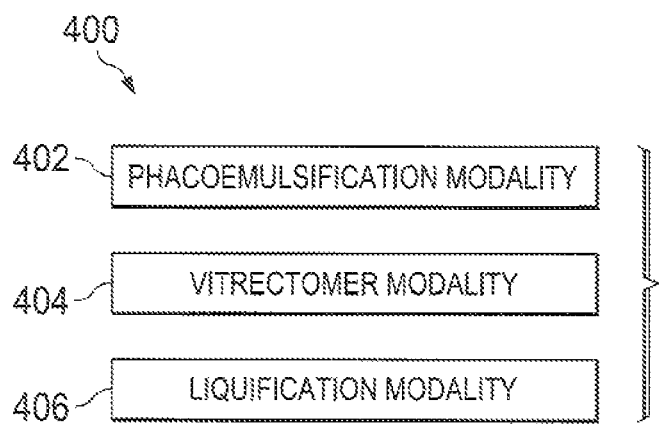
FIG. 4 is an illustration of an exemplary graphical user interface for the emulsification surgical console of FIG. 1.

At 302, a user may identify a particular surgical modality to be carried out with the console 100. FIG. 4 shows an exemplary user interface 400 for identifying a particular surgical modality. The user interface 400 may be displayed on the display screen 104 of the console 100, and provides a listing of modalities selectable by a user. In this example, the selectable modalities include a phacoemulsification modality 402, a vitrectomer modality 404, and a liquification modality 406, such as an AQUALASE® modality. In other embodiments, other modalities also are preprogrammed into the surgical console 100. In this example, the phacoemulsification modality 402 is identified as being selected.

Returning to FIG. 3, at 304, the user identifies a first subsystem to monitor for a triggering event and a second subsystem to respond to the triggering event. Since not every subsystem in the console 100 is used with each modality, the subsystems available for identification at 304 may be dependent on the modality selected at 302. For example, the ultrasonic generator subsystem may be displayed on the display screen 104 when the phacoemulsification modality 402 is selected at 302, but may not be displayed when the vitrectomer modality 406 is selected at 302.

Regardless of the modality selected, at 304, the user identifies a first subsystem to monitor for a triggering event and a second subsystem to respond to the triggering event. This is described in greater detail with reference to FIG. 5.

Figure 5:
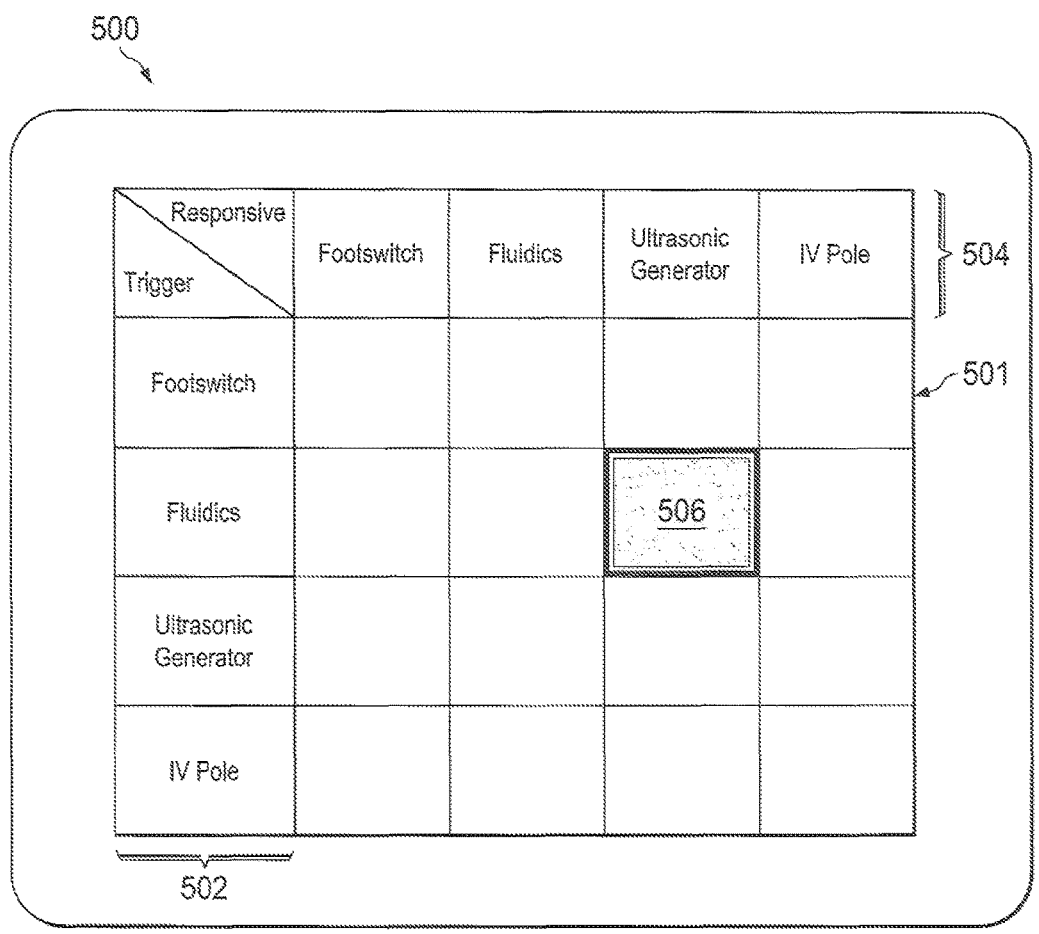
FIG. 5 is an illustration of an exemplary graphical user interface for the emulsification surgical console of FIG. 1 after selecting a selectable option in FIG. 4.

FIG. 5 shows an exemplary user interface 500 for controlling relationships between subsystems in the phacoemulsification modality on the surgical console 100 shown in FIG. 1. Particularly, the exemplary interface in FIG. 5 permits a user to easily identify a first subsystem to monitor for a triggering event and a second subsystem to respond to the triggering event in accordance with 304 in FIG. 3. The user interface 500 may be displayed on the display screen 104 in FIG. 1 for convenient viewing and access by the user.

The exemplary user interface 500 includes a matrix 501 of selectable cells displayed in a table format with a left column 502 listing subsystems to be identified for a triggering event and a top row 504 listing subsystems to respond to the triggering event. In this example, the listings of subsystems correspond to those used in an emulsification modality 402 as selected at 302 in FIG. 3 and as discussed above. Particularly, the subsystems in each of the left column 502 and the top row 504 identify the subsystems footswitch, fluidics, ultrasonic generator, and IV pole. However, when alternative modalities are selected at 302, other subsystems that correspond to the selected modality may be displayed on the interface 500 at 304. For example, when the vitrectomer modality 404 is selected at 302, the interface 500 displays an option including the vitrectomy cutter subsystem and does not display the ultrasonic generator subsystem.

In FIG. 5, a user may identify and select a cell in the matrix 501 that corresponds to the desired triggering event subsystem and the desired responsive subsystem. In the example shown, a user selects the desired event subsystem and the desired responsive subsystem simultaneously by identifying the cell at the intersection of a subsystem row and a subsystem column. Here, an exemplary cell 506 identifies the intersection of the fluidics row as the triggering event subsystem and the ultrasonic generator column as the responsive subsystem. In embodiments using a touch screen as an input device, the user may directly select the desired cell at the intersection of the event subsystem and the desired responsive subsystem. The selected cell may be highlighted as is cell 506. Other input devices allow a user to scroll through the cell or point and click, using methods known in the art.

Using the matrix 501 in FIG. 5, or other selection system, a user may select any desired event triggering subsystem and any desired responsive subsystem. In the embodiment shown, the user may select the same subsystem to be both the event subsystem and the responsive subsystem. For example, by selecting the cell at the intersection of the fluidics row and the fluidics column, the user is able to configure the fluidics subsystem to respond in a desired manner when a triggering event occurs in the fluidics subsystem.

Figure 6:
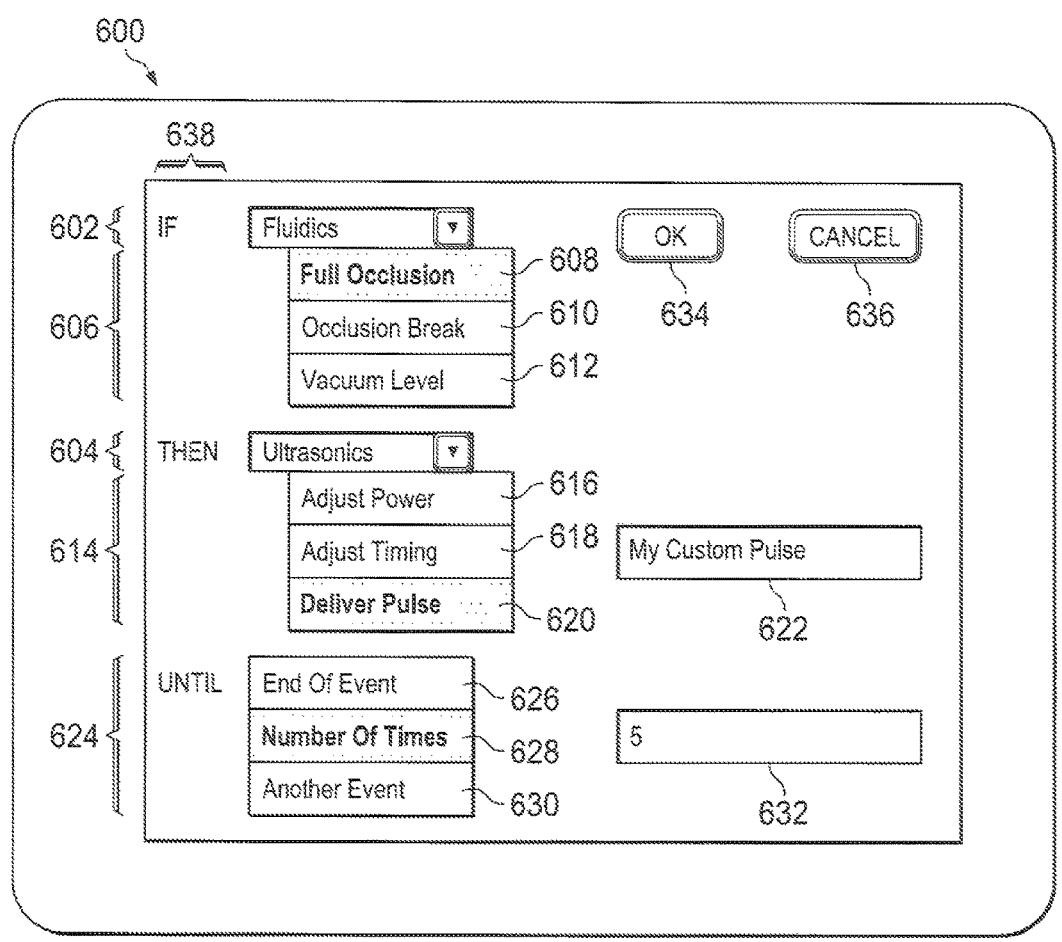
FIG. 6 is an illustration of an exemplary graphical user interface for the emulsification surgical console of FIG. 1 after selecting a selectable option in FIG. 5.

Returning now to FIG. 3, once a user identifies a first subsystem to monitor for a triggering event and a second subsystem at 304, the user inputs a triggering event in the first subsystem and a result to be achieved on the second subsystem at 306 and 308 respectively (e.g., see FIG. 6 for additional description of 306 and 308).

FIG. 6 shows an exemplary user interface 600 for selecting both a triggering event and a responsive result. Continuing with the example shown in FIG. 5, the fluidics subsystem was selected as the event triggering subsystem and the ultrasonic generator was selected as the responsive subsystem. These are shown and displayed on the interface as identified by the reference numerals 602 and 604, respectively. The user interface 600 provides a series of selectable options 606 that represent triggering events or conditions that may potentially or selectively occur at the identified triggering subsystem 602 during the surgical procedure. These events, while not unexpected, are generally not considered a part of the regular procedure. In the example shown, when the fluids subsystem is the triggering subsystem 602 and the ultrasonic generator is the responsive subsystem 604, then the selectable events include a full occlusion option 608, an occlusion break option 610, and vacuum level option 612 that refers to vacuum pressure exceeding or falling below set thresholds. In this example, the full occlusion event 608 is highlighted as having been selected as the triggering event in the triggering subsystem 602.

In addition to displaying selectable triggering events, the interface 600 also displays selectable responsive results 614. In this case, when the ultrasonic generator subsystem is the responsive subsystem 604 and the fluidics subsystem is the triggering subsystem 602, the selectable responsive results 614 include an adjust power option 616, an adjust timing option 618, and a deliver pulse option 620. Here, the deliver pulse option 620 is highlighted as having been selected as the responsive event in the responsive subsystem 604. Therefore, in response to the input triggering event of full occlusion 608 at the first fluidics subsystem, instead of continuing with the original preprogrammed relationship, the ultrasonic generator subsystem deviates from the original preprogramming and delivers an ultrasonic pulse 620.

In this example, when the selectable deliver pulse option 620 is selected as the responsive result, the user is permitted to input a custom feature adjustment 622, which in this case is a custom ultrasonic pulse. For example, a custom pulse may include increasing the ultrasonic power by a specified or preset amount for a preset period of time. Likewise, if the adjust power option 616 or the adjust timing option 618 were selected, the user interface may, in some examples, permit a user to input a custom feature adjustment 622 that includes increasing or decreasing a desired power level or a desired timing adjustment. In some examples, these custom feature adjustments 622 are limited to specific adjustment range.

Returning to FIG. 3, a user may input ending criteria for the responsive result at 310. Again, this is described with reference to FIG. 6. FIG. 6 includes a listing of selectable ending criteria options 624. The ending criteria options 624 permit a user to indicate when the responsive subsystem 604 should end its responsive action 614. In this example, the ending criteria options 624 include an end of event option 626, a number of times option 628, and an another event option 630. Accordingly, so long as the triggering event 606 occurs at the first triggering subsystem 602, the responsive result 614 at the second responsive subsystem 604 occurs until the ending criteria 624 are met. In this case, the number of items option 628 is shown as having been selected and a user can select a specific number of pulses to be delivered by the responsive subsystem 604, at the box 632. Here, the user has selected "5" as the number of times a pulse will be generated in response to the triggering event.

To activate the modified relationship between the first and second subsystems, the user may select an enter or submit option, identified here as a selectable OK option 634. Alternatively, a user can cancel the modified relationship by selecting a cancel option 636 in FIG. 6.

In this example, instructive wording or instructions may assist a user in establishing the desired relationship between the triggering event subsystem 602 and the responsive subsystem 604. For example, the user interface in FIG. 6 recites an IF-THEN-UNTIL statement 638 using the first and second subsystems and the ending criteria as the structure for the statement.

In the example shown, the available options for each subsystem relationship are preprogrammed into the console 100. Because of this, only certain selectable options are available for each combination of subsystems. In addition, the console 100 may limit a user's ability to modify the program beyond preset parameters. Each preset parameter may include a range within which the subsystem relationships may be modified, but may include limits beyond which the subsystem relationships may not be modified. In this way, although a user may make modifications to relationships between subsystems, the user may be restricted from modifying the relationships in a way that might inadvertently cause damage, such as severe corneal burns, during a surgical procedure. In accordance, with this, the responsive results for each responsive subsystem may be limited to specific selectable results that have been found to be within a range of safe adjustments. For example, in some embodiments, the number of times that a pulse may be delivered as a response to a triggering event may be limited to be within a range of 1-10. Likewise, the adjust power option may be limited to permit a user to increase or decrease power by no more than 10% of its preprogrammed settings. Other safety limits for other responsive results also may be included.

Figure 7:
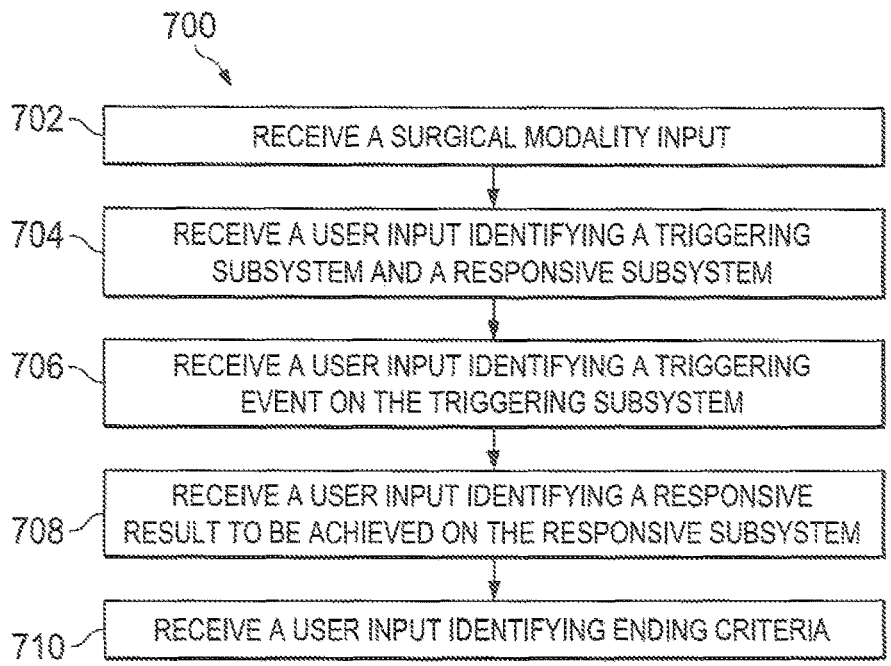
FIGS. 7 and 8 are exemplary flow diagrams illustrating exemplary methods of operation performed by the emulsification surgical console of FIG. 1

FIG. 7 is a flow chart detailing an exemplary method 700 carried out by the computer system 103 of the console 100. Although the method 700 is written from a computer perspective, much of the discussion and methods described above are equally applicable to the method of FIG. 7. Accordingly, in order to avoid duplication, those portions are not repeated here.

At 702, the console 100 may receive a surgical modality input at the user interface 400 (e.g., see FIG. 4) on the display screen 104. Based upon the received modality, the user interface generates a pop-up or follow-up screen, shown as interface 500 in FIG. 5.

At a 704, the console 100 receives a user input identifying a triggering subsystem and a responsive subsystem. In the example in FIG. 5, the triggering subsystem is the fluidics subsystem and the responsive subsystem is the ultrasonic generator subsystem. Although shown as being simultaneously selectable in FIG. 5, in some examples, the triggering and responsive subsystems are separately selected. Upon selection of the triggering and responsive subsystems, the user interface generates a pop-up or follow-up screen, shown as interface 600 in FIG. 6. In the exemplary interface shown in FIG. 6, the triggering and responsive subsystems are displayed adjacent a number of selectable triggering events and responsive results. At 706, the console 100 receives a user input identifying a triggering event on the triggering subsystem. At 708, the console 100 receives a user input identifying a responsive result to be achieved on the responsive subsystem. At 710, the console 100 receives a user input identifying ending criteria. Upon selection of the activate option, shown as the ok option in FIG. 6, the console 100 operates based on the modified relationship between the triggering subsystem and the responsive subsystem.

Figure 8:
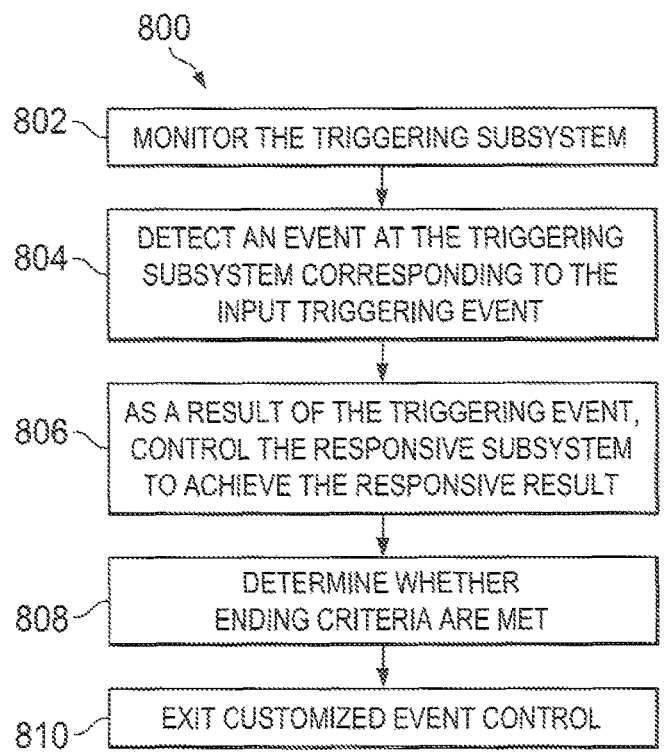

FIG. 8 is a flow chart detailing an exemplary method 800 of system operation after the preprogrammed operation of console 100 has been adjusted or modified based on the methods and systems in this disclosure. In this example, during operation, the console 100 monitors the triggering subsystem for events that correspond with the input triggering event at 802. Using the configuration detailed in FIG. 5 as an example, the console monitors the fluidics subsystem for the triggering event of full occlusion.

At 804, the console 100 detects the event at the triggering subsystem corresponding to the input triggering event. At 806, as a result of the triggering event, the console 100 controls the responsive subsystem to achieve the desired responsive result. Again referring to the example in FIG. 5, the console 100 controls the ultrasonic generator subsystem as a result of the detected full occlusion at the fluidics subsystem. In this case controlling the ultrasonic generator as a responsive result of the full occlusion includes delivering a ultrasonic pulse as customized by the user.

At 808, the console 100 determines whether the ending criteria are met. Referring to FIG. 5, the ending criteria is met when the pulse is delivered five times. Accordingly, after delivering the pulse five items, the console 100 exits the customized event control and returns to its original preprogrammed control, as indicated at 510. It operates under the original programmed control until the console 100 detects a new triggering event.

The console 100 permits a user to enter and store any number of desired response and triggering event scenarios. Since the console 100 simultaneously operates multiple subsystems, the system also simultaneously monitors for any number of triggering events among any number of subsystems, and may respond to those triggering events with the respective, associated responsive result. Accordingly, during operation, the system may execute any number of scenarios in parallel, or in series, during a given procedure.

Alternative examples of the method and system for modifying a preprogrammed relationship between subsystems allow a user to select the triggering subsystem and the responsive subsystem in series, instead of selecting them simultaneously as described with reference to FIG. 5. Accordingly, instead of having a simple matrix of selectable relationships as shown in FIG. 5, the user may select a triggering subsystem from, for example, a drop-down menu. When the triggering subsystem is selected, the console may permit a user to select a triggering event from a second drop down menu. After selecting the triggering subsystem and either before or after selecting the triggering event, the user may select the responsive subsystem. This could be, for example, from a drop down menu or other selection. A user may then select a responsive result to the triggering event, and may select ending criteria for the responsive result. The method elements may be carried out in an order other than that described.

In some examples, a user does not perform identifying the subsystem separately from selecting the triggering event. In one example of this, the interface includes a listing of all available triggering events and a second listing of all available responses to the triggering events. A separate listing may include all the available ending criteria. A user may select a triggering event, a response, and ending criteria, thereby modifying or adjusting the relationship between the different subsystems for the selected triggering event.

In some examples, a user may enter more than one responsive result to each triggering event. For example, in response to a full occlusion at the fluidics subsystem, a user may enter both the responsive results of adjusting the power to the ultrasonic generator subsystem and simultaneously decreasing the fluid pump flow at the fluidics subsystem. In other examples, the user may enter more than one triggering event for a responsive result. For example, the user may configure the triggering event to require both full occlusion at the fluidics subsystem and vacuum level at the fluidics subsystem before a pulse is delivered by the ultrasonic generator subsystem.

It is worth noting that although the interfaces 400, 500, and 600 are identified as separate interfaces displayable on the display screen 104 on the console 100, these may be considered a single interface comprising a plurality of screen images.

In addition, some examples include multiple triggering events and responsive results in series. In such console systems, a user may identify a first subsystem and triggering event with a second responsive subsystem and responsive action and may further identify a third subsystem and triggering event that may occur during the response of the second subsystem. Accordingly, a fourth responsive result will occur as a result of the triggering event at the third subsystem.

Some examples of modified preprogrammed relationships between a plurality of subsystems of a surgical console are provided below. As discussed, the user interface may be used in the manner described to create these modifications.

1—IF the fluidics subsystem indicates a vacuum level above a certain threshold THEN increase the ultrasonic generator power level by a specified amount for a user defined duration after which restore the ultrasonic generator power level, assuming the user is using the phacoemulsification modality of the console.

2—IF the fluidics subsystem indicates a vacuum level above a certain threshold THEN increase the liquification or AQUALASE® power level by a specified amount for a user defined duration after which restore the liquification or AQUALASE® power level, assuming the user is using the liquification or AQUALASE® modality of the console.

3—IF the fluidics subsystem indicates a vacuum level above a certain threshold THEN increase the vitrectomer cut rate by a specified amount for a user defined duration after which restore the vitrectomer cut rate, assuming the user is using the vitrectomer modality of the console.

4—IF the fluidics subsystem indicates an occlusion break THEN reverse the direction of the fluidics pump (reflux) by a user configurable amount.

Some embodiments of the consoles disclosed herein require identification before granting access to the configurable interface. For example, the interface may be password protected to limit access to only individuals who use the console or have become certified by completing training. Furthermore, some consoles grant different levels of access depending on the settings of the console. For example, a level one user may have only limited modification options, while a level two user may have additional modification options.

In some examples, the levels of access are based on subscriptions. For example, for a yearly subscription fee, users may be granted one of a number of plans such as a base plan, a premium plan, or an elite plan. The base plan may offer a limited level of customization. The premium plan may offer a limited number of pulse options and provide for limited configuration. An elite plan may offer an unlimited number of pulse patterns, unlimited configuration, and may grant e-connectivity with the ability to share and publish configurations.

In some examples, users may share or publish their configurations on a restricted or public-domain website so that others can benefit from their settings. In some examples the website allows the user to add a description, including verbiage and multimedia, of the configuration along with supporting clinical trials data to confirm the usefulness of each particular configuration.

The foregoing has outlined features of several embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions or techniques do not depart from the spirit and scope of the present disclosure, and that they may make various changes, substitutions and alterations herein without departing from the spirit and scope of the present disclosure.

What is claimed is:

1. A graphical user interface presented on a system display screen, the graphical user interface comprising:
a representation listing, shown on the display screen, of at least two of a plurality of subsystems of a surgical system, the representation listing configured for a user to select, through user interaction with the graphical user interface, a desired event triggering subsystem representation and a desired responsive subsystem representation;

a plurality of user-selectable triggering event representations shown on the display screen, each of the plurality of user-selectable triggering event representations identifying a subsystem condition that occurs during a surgical procedure performed with the surgical system, the plurality of user-selectable triggering event representations configured for the user to select, through user interaction with the graphical user interface, a user-selected triggering event; and a plurality of user-selectable response representations, shown on the display screen, to the plurality of user-selectable triggering event representations, the plurality of user-selectable response representations configured for the user to select, through user interaction with the graphical user interface, a user-selected response representation, the user-selectable response representations representing user-selectable subsystem responses to perform when the user-selected triggering event is detected, wherein the user-selectable subsystem responses deviate from preprogrammed relationships between subsystems of the surgical system;

one or more user-selectable ending criteria representations, shown on the display screen, for one or more of the plurality of user-selectable response representations, the one or more user-selectable ending criteria representations configured for the user to select, through user interaction with the graphical user interface, a user-selected ending criteria, the ending criteria representations identifying one or more conditions for ending the user-selected response to the user-selected triggering event and resuming control of the subsystems based on the preprogrammed relationships, wherein user interaction with the graphical user interface comprises the user selecting a graphical representation on the graphical user interface through a surgical system input device.

2. The graphical user interface of claim 1, wherein the interface enables the user to simultaneously select the desired event triggering subsystem representation and the desired responsive subsystem representation.

3. The graphical user interface of claim 1, wherein the representation listing of the plurality of subsystems of the surgical system is in the form of a matrix including an event triggering subsystem list and responsive subsystem list, a user-selectable cell in the matrix identifying both an event triggering subsystem from the event triggering subsystem list and a responsive subsystem from the responsive subsystems list such that selection of the cell, through user interaction with the graphical user interface, enables the user to simultaneously select the desired event triggering subsystem and the desired responsive subsystem.

4. The graphical user interface of claim 1, wherein the plurality of subsystems of the surgical system, represented in the representation listing on the graphical user interface, comprise a footpedal subsystem, a fluidics subsystem that comprises an aspiration vacuum, an ultrasonic generator subsystem that comprises an ultrasonic oscillation handpiece, and an intravenous (IV) pole subsystem.

5. The graphical user interface of claim 1, wherein one or more of the user-selectable response representations includes an associated level adjustment enabling the user to adjust the response within a preprogrammed range.

6. The graphical user interface of claim 1, wherein the graphical user interface is configured for the user to select a footswitch subsystem, through user interaction with the graphical user interface, as a desired event triggering subsystem and a fluidics subsystem, which comprises an aspiration vacuum, as a desired responsive subsystem.

7. The graphical user interface of claim 1, wherein the graphical user interface is configured for the user to select a footswitch subsystem, through user interaction with the graphical user interface, as a desired event triggering subsystem and an ultrasonic generator subsystem, which comprises an ultrasonic oscillation handpiece, as a desired responsive subsystem.

8. The graphical user interface of claim 1, wherein the graphical user interface is configured for the user to select, through user interaction with the graphical user interface, a footswitch subsystem as a desired event triggering subsystem and an intravenous (IV) pole subsystem as a desired responsive subsystem.

9. The graphical user interface of claim 1, wherein the graphical user interface is configured for the user to select, through user interaction with the graphical user interface, an ultrasonic generator subsystem, which comprises an ultrasonic oscillation handpiece, as a desired event triggering subsystem and a fluidics subsystem, which comprises an aspiration vacuum, as a desired responsive subsystem.

10. The graphical user interface of claim 1, wherein the graphical user interface is configured for the user to select, through user interaction with the graphical user interface, an intravenous (IV) pole subsystem as a desired event triggering subsystem and a fluidics subsystem, which comprises an aspiration vacuum, as a desired responsive subsystem.

11. The graphical user interface of claim 1, wherein the graphical user interface is configured for the user to select, through user interaction with the graphical user interface, a fluidics subsystem, which comprises an aspiration vacuum, as a desired event triggering subsystem and a footswitch subsystem as a desired responsive subsystem.

12. The graphical user interface of claim 1, wherein the graphical user interface is configured for the user to select, through user interaction with the graphical user interface, an ultrasonic generator subsystem, which comprises an ultrasonic oscillation handpiece, as a desired event triggering subsystem and a footswitch subsystem as a desired responsive subsystem.

13. The graphical user interface of claim 1, wherein the graphical user interface is configured for the user to select, through user interaction with the graphical user interface, an intravenous (IV) pole subsystem as a desired event triggering subsystem and a footswitch subsystem as a desired responsive subsystem.

14. The graphical user interface of claim 1, wherein the graphical user interface is configured for the user to select, through user interaction with the graphical user interface, an ultrasonic generator subsystem, which comprises an ultrasonic oscillation handpiece, as a desired event triggering subsystem and an intravenous (IV) pole subsystem as a desired responsive subsystem.

15. The graphical user interface of claim 1, wherein the graphical user interface is configured for the user to select, through user interaction with the graphical user interface, a fluidics subsystem, which comprises an aspiration vacuum, as a desired event triggering subsystem and an intravenous (IV) pole subsystem as a desired responsive subsystem.

16. The graphical user interface of claim 1, wherein the graphical user interface is configured for the user to select, through user interaction with the graphical user interface, an intravenous (IV) pole subsystem as a desired event triggering subsystem and an ultrasonic generator subsystem, which comprises an ultrasonic oscillation handpiece, as a desired responsive subsystem.

17. The graphical user interface of claim 1, wherein the graphical user interface is configured for the user to select, through user interaction with the graphical user interface, a fluidics subsystem, which comprises an aspiration vacuum, as a desired event triggering subsystem and an ultrasonic generator subsystem, which comprises an ultrasonic oscillation handpiece, as a desired responsive subsystem.

18. The graphical user interface of claim 1, wherein the desired event triggering subsystem representation or the desired responsive subsystem representation corresponds to a vitrectomy cutter subsystem that includes a vitrectomy handpiece.

19. The graphical user interface of claim 1,
wherein the preprogrammed relationships between subsystems of the surgical system are configured to perform an emulsification surgical procedure; and
wherein the user selects, through user interaction with the graphical user interface, the desired event triggering subsystem representation, the desired responsive subsystem representation, the user-selectable triggering event representation, the user-selectable response representation, and the user-selectable ending criteria representation before beginning a surgical procedure that corresponds to the selected desired event triggering subsystem representation, the desired responsive subsystem representation, the user-selectable triggering event representation, the user-selectable response representation, and the user-selectable ending criteria representation.

20. The graphical user interface of claim 1, wherein the user selects the desired event triggering subsystem representation, the desired responsive subsystem representation, the user-selectable triggering event representation, the user-selectable response representation, and the user-selectable ending criteria representation through use of a touch screen, keyboard, mouse, or trackball to interact with the graphical user interface.

* * * * *